(12) United States Patent
Li et al.

(10) Patent No.: US 10,982,098 B2
(45) Date of Patent: Apr. 20, 2021

(54) COMPOSITIONS AND METHODS FOR THE MODIFICATION OF IMINE COVALENT ORGANIC FRAMEWORKS (COFS)

(71) Applicants: Xinle Li, Albany, CA (US); Yi Liu, Fremont, CA (US)

(72) Inventors: Xinle Li, Albany, CA (US); Yi Liu, Fremont, CA (US)

(73) Assignee: The Regents of the University of California, Oakland, CA (US)

(*) Notice: Subject to any disclaimer, the term of this patent is extended or adjusted under 35 U.S.C. 154(b) by 147 days.

(21) Appl. No.: 16/206,979

(22) Filed: Nov. 30, 2018

(65) Prior Publication Data

US 2019/0161623 A1    May 30, 2019

Related U.S. Application Data

(60) Provisional application No. 62/592,561, filed on Nov. 30, 2017.

(51) Int. Cl.
| | |
|---|---|
| *C09D 5/00* | (2006.01) |
| *C08L 79/04* | (2006.01) |
| *C08G 83/00* | (2006.01) |
| *C07D 471/22* | (2006.01) |

(52) U.S. Cl.
CPC ............ *C09D 5/00* (2013.01); *C07D 471/22* (2013.01); *C08G 83/00* (2013.01); *C08L 79/04* (2013.01)

(58) Field of Classification Search
None
See application file for complete search history.

(56) References Cited

U.S. PATENT DOCUMENTS

| | | |
|---|---|---|
| 2010/0043636 A1 | 2/2010 | Hwang et al. |
| 2010/0143693 A1 | 6/2010 | Yaghi et al. |
| 2011/0236301 A1 | 9/2011 | Kang et al. |
| 2013/0327716 A1* | 12/2013 | George .................. B09C 1/06 210/671 |
| 2014/0037944 A1 | 2/2014 | Dichtel et al. |
| 2014/0148596 A1 | 5/2014 | Dichtel et al. |
| 2015/0266885 A1 | 9/2015 | Banerjee et al. |
| 2015/0299147 A1 | 10/2015 | Banerjee et al. |
| 2016/0376282 A1 | 12/2016 | Banerjee et al. |
| 2017/0130349 A1 | 5/2017 | Ramanathan et al. |
| 2017/0314737 A1* | 11/2017 | Sozzani ................ B01J 20/267 |
| 2017/0362190 A1 | 12/2017 | Banerjee et al. |

(Continued)

OTHER PUBLICATIONS

Diercks et al., "The atom, the molecule, and the covalent organic framework." Science 355, eaal1585 (2017).

(Continued)

*Primary Examiner* — Ramsey Zacharia
(74) *Attorney, Agent, or Firm* — Robin C. Chiang; Lawrence Berkeley National Laboratory

(57) ABSTRACT

The present invention provides for a method for modifying a covalent organic framework (COF), the method comprising: contacting a COF comprising an imine group with a phenylacetylene in, or to form, a mixture, in a suitable reaction condition for converting the imine group into a quinoline group, and COF comprising a quinoline group. The present invention also provides for a superhydrophobic surface comprising a solid surface coated with or comprising the covalent organic framework (COF).

9 Claims, 10 Drawing Sheets

(56) References Cited

U.S. PATENT DOCUMENTS

2018/0272313 A1 9/2018 Shim et al.
2018/0319821 A1 11/2018 Yaghi et al.

OTHER PUBLICATIONS

Furukawa et al., "Storage of hydrogen, methane, and carbon dioxide in highly porous covalent organic frameworks for clean energy applications." J. Am. Chem. Soc. 131, 8875-8883 (2009).
Oh et al., "A cryogenically flexible covalent organic framework for efficient hydrogen isotope separation by quantum sieving." Angew. Chem. Int. Ed. 52, 13219-13222 (2013).
Ding et al., "Thioether-based fluorescent covalent organic framework for selective detection and facile removal of mercury (II)." J. Am. Chem. Soc. 138, 3031-3037 (2016).
Lu et al., "Synthesis of ultrafine and highly dispersed metal nanoparticles confined in a thioether-containing covalent organic framework and their catalytic applications." J. Am. Chem. Soc. 139, 17082-17088 (2017).
Wan et al., "A belt-shaped, blue luminescent, and semiconducting covalent organic framework." Angew. Chem. Int. Ed. 47, 8826-8830 (2008).
DeBlase et al., "β-Ketoenamine-linked covalent organic frameworks capable of pseudocapacitive energy storage." J. Am. Chem. Soc. 135, 16821-16824 (2013).
Jin et al., "Tessellated multiporous two-dimensional covalent frameworks." Nat. Rev. Chem. 1, 0056 (2017).
Huang et al., "Multiple-component covalent organic frameworks." Nat. Commun. 7, 12325 (2016).
Cote et al., "Porous, crystalline, covalent organic frameworks." Science 310, 1166-1170 (2005).
Cote et al., "Reticular synthesis of microporous and mesoporous 2D covalent organic frameworks." J. Am. Chem. Soc. 129, 12914-12915 (2007).
Wan et al., "A photoconductive covalent organic framework: self-condensed arene cubes composed of eclipsed 2D polypyrene sheets for photocurrent generation." Angew. Chem. Int. Ed. 48, 5439-5442 (2009).
Segura et al., "Covalent organic frameworks based on Schiftbase chemistry: synthesis, properties and potential applications." Chem. Soc. Rev. 45, 5635-5671 (2016).
Qian et al., "Toward covalent organic frameworks bearing three different kinds of pores: the strategy for construction and COF-to-COF transformation via heterogeneous linker exchange." J. Am. Chem. Soc. 139, 6736-6743 (2017).
Kandambeth et al., "Construction of crystalline 2D covalent organic frameworks with remarkable chemical (acid/base) stability via a combined reversible and irreversible route." J. Am. Chem. Soc. 134, 19524-19527 (2012).
Kandambeth et al., "Enhancement of chemical stability and crystallinity in porphyrin-containing covalent organic frameworks by intramolecular hydrogen bonds." Angew. Chem. Int. Ed. 52, 13052-13056 (2013).
Chen et al., "Locking covalent organic frameworks with hydrogen bonds: general and remarkable effects on crystalline structure, physical properties, and photochemical activity." J. Am. Chem. Soc. 137, 3241-3247 (2015).
Wei et al., "Benzoxazole-linked ultrastable covalent organic frameworks for photocatalysis." J. Am. Chem. Soc. 140, 4623-4631 (2018).
Halder et al., "Ultrastable imine-based covalent organic frameworks for sulfuric acid recovery: an effect of interlayer hydrogen bonding." Angew. Chem. Int. Ed. 57, 5797-5802 (2018).
Xu et al., "Conjugated microporous polymers: design, synthesis and application." Chem. Soc. Rev. 42, 8012-8031 (2013).
Rao et al., "Conjugated covalent organic frameworks via michael addition—elimination." J. Am. Chem. Soc. 139, 2421-2427 (2017).
Liu et al., "A two-dimensional conjugated aromatic polymer via C—C coupling reaction." Nat. Chem. 9, 563 (2017).
Liu et al., "Solution synthesis of semiconducting two-dimensional polymer via trimerization of carbonitrile." J. Am. Chem. Soc. 139, 11666-11669 (2017).
Jin et al., "Two-dimensional sp2 carbon—conjugated covalent organic frameworks." Science 357, 673-676 (2017).
Nagai et al., "Pore surface engineering in covalent organic frameworks." Nat. Commun. 2, 536 (2011).
Huang et al., "Tailor-made pore surface engineering in covalent organic frameworks: systematic functionalization for performance screening." J. Am. Chem. Soc. 137, 7079-7082 (2015).
Khayum et al., "Chemically delaminated free-standing ultrathin covalent organic nanosheets." Angew. Chem. Int. Ed. 55, 15604-15608 (2016).
Lohse et al., "Sequential pore wall modification in a covalent organic framework for application in lactic acid adsorption." Chem. Mater 28, 626-631 (2016).
Waller et al., "Chemical conversion of linkages in covalent organic frameworks." J. Am. Chem. Soc. 138, 15519-15522 (2016).
Dibble et al., "An Aza-Diels—Alder route to polyquinolines." Macromolecules 48, 557-561 (2015).
Xu et al., "Stable, crystalline, porous, covalent organic frameworks as a platform for chiral organocatalysts." Nat. Chem. 7, 905 (2015).
Hu et al., "Probing the chemical structure of monolayer covalent-organic frameworks grown via Schiff-base condensation reactions." ChemComm 52, 9941-9944 (2016).
Gammon et al., "Experimental comparison of N (1s) Xray photoelectron spectroscopy binding energies of hard and elastic amorphous carbon nitride films with reference organic compounds." Carbon N. Y. 41, 1917-1923 (2003).
Zhu et al., "Unravelling surface and interfacial structures of a metal-organic framework by transmission electron microscopy." Nat. Mater. 16, 532-536 (2017).
Medina et al., "Oriented thin films of a benzodithiophene covalent organic framework" ACS Nano 8, 4042-4052 (2014).
Ascherl et al., "Molecular docking sites designed for the generation of highly crystalline covalent organic frameworks." Nat. Chem. 8, 310-316 (2016).
Peng et al., "Ultrathin two-dimensional covalent organic framework nanosheets: preparation and application in highly sensitive and selective DNA detection." J. Am. Chem. Soc. 139, 8698-8704 (2017).
Bai et al., "Nanoscale covalent organic frameworks as smart carriers for drug delivery." ChemComm 52, 4128-4131 (2016).
Mullangi et al., "Superhydrophobic covalent organic frameworks for chemical resistant coatings and hydrophobic paper and textile composites." J. Mater. Chem. A 5, 8376-8384 (2017).
Zhang et al., "A facile and general coating approach to moisture/water-resistant metal-organic frameworks with intact porosity." J. Am. Chem. Soc. 136, 16978-16981 (2014).
Nguyen et al., "Moisture-resistant and superhydrophobic metal-organic frameworks obtained via postsynthetic modification." J. Am. Chem. Soc. 132, 4560-4561 (2010).
Uribe-Romo et al. "A Crystalline Imine-Linked 3-D Porous Covalent Organic Framework", J. Am. Chem. Soc. 131:4570-4571 (2009).

\* cited by examiner

US 10,982,098 B2

COMPOSITIONS AND METHODS FOR THE MODIFICATION OF IMINE COVALENT ORGANIC FRAMEWORKS (COFS)

CROSS-REFERENCE TO RELATED APPLICATIONS

This application claims priority to U.S. Provisional Patent Application Ser. No. 62/592,561, filed on Nov. 30, 2017, which is hereby incorporated by reference.

STATEMENT OF GOVERNMENTAL SUPPORT

The invention was made with government support under Contract Nos. DE-AC02-05CH11231 awarded by the U.S. Department of Energy. The government has certain rights in the invention.

FIELD OF THE INVENTION

The present invention is in the field of covalent organic frameworks (COFs).

BACKGROUND OF THE INVENTION

Covalent organic frameworks (COFs) are porous, crystalline networks constructed by linking molecular organic building units with covalent bonds[1]. Owing to their high surface area, chemical diversity, and tunable functionality, COFs have been adopted as an auspicious platform for a plethora of applications pertaining to gas adsorption[2], separation[3], chemical sensing[4], catalysis[5], optoelectronics[6], and energy storage[7]. In order to establish a covalently linked periodic framework in COFs, current methods rely on the reversible covalent bond formation to connect multivalent monomers through thermodynamic equilibria[8,9]. This inherent reversibility of the linkages within COFs, however, severely limit fundamental materials properties such as environmental stability towards solvents and chemicals, thus constraining their practical applications. For example, COFs with boroxine linkages are susceptible to water or protic solvents[10,11,12]. COFs based on a more robust linkage, such as the C=N imine bond, represent the prevalent class of COFs that show improved hydrothermal stability[13]. The chemical stability of most imine COFs is however still far from satisfactory since they undergo hydrolysis under strongly acidic conditions or exchange with amines due to the reversible nature of imine[14]. As such, a facile methodology that enables the fabrication of chemically robust COFs is much desired[15,16,17,18,19].

SUMMARY OF THE INVENTION

The present invention provides for a method for modifying a covalent organic framework (COF), the method comprising: (a) contacting a COF comprising an imine group with a phenylacetylene in, or to form, a mixture, in a suitable reaction condition for converting the imine group into a quinoline group, (b) optionally heating the COF comprising an imine group and the phenylacetylene (such as for about one to about three days), (c) optionally cooling the mixture, (d) optionally separating or isolating a solid precipitate formed from the rest of the mixture, (e) optionally washing the mixture and/or the separated or isolated solid precipitate with a second organic solvent (such as tetrahydrofuran (THF)).

The present invention provides for a covalent organic framework (COF) comprising a quinoline group. In some embodiments, the COF does not comprise any imine group. In some embodiments, the COF is a product of the method of the present invention. The present invention provides for a composition comprising: (a) a covalent organic framework (COF) comprising an imine group, and (b) a phenylacetylene.

A superhydrophobic surface comprising a solid surface coated with or comprising the covalent organic framework (COF) of the present invention.

A superhydrophobic material comprising: an exposed surface comprising the covalent organic framework (COF) of the present invention.

BRIEF DESCRIPTION OF THE DRAWINGS

The foregoing aspects and others will be readily appreciated by the skilled artisan from the following description of illustrative embodiments when read in conjunction with the accompanying drawings.

FIG. 3D. HRTEM characterization of COF-1 and MF-1a. The Fourier-filtered image of the selected red square area (scale bar, 5 nm), Inset: FFT from the red square on the MF-1a.

DETAILED DESCRIPTION OF THE INVENTION

Figure 1A:
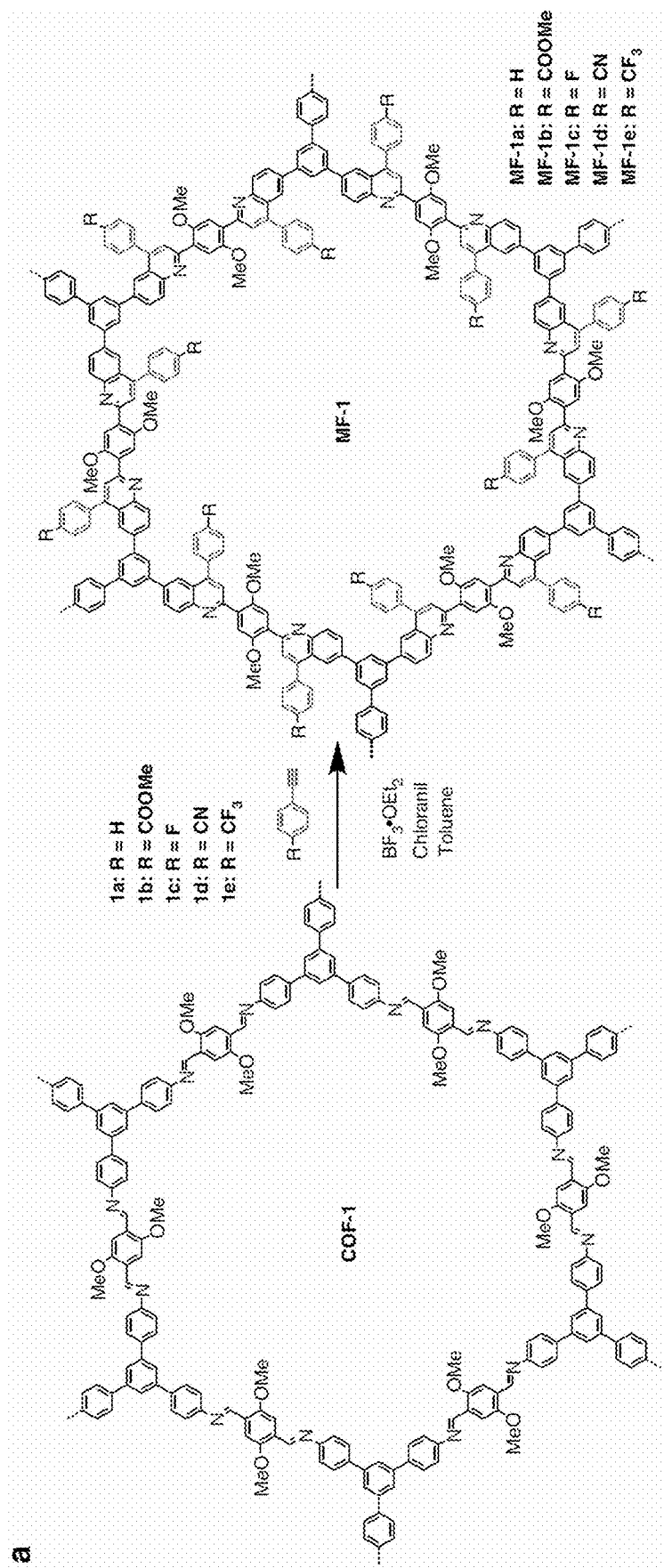
FIG. 1A. Post-synthetic modification of COFs via aza-DA reaction. The reaction scheme showing the transformation of one lattice unit of COF-1 into MF-1a-e.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

As used in the specification and the appended claims, the singular forms "a," "an," and "the" include plural referents unless the context clearly dictates otherwise. Thus, for example, reference to a "framework" includes a single framework as well as a plurality of frameworks, either the same or different.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

The term "about" refers to a value including 10% more than the stated value and 10% less than the stated value.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The present invention provides for a general method to make porous and multifunctional covalent organic framework (COFs). COFs are a class of crystalline, porous organic material that is light weight and has very high surface area. It has many applications such as for gas adsorption/desorption, catalysis, CO$_2$ reduction, environmental decontamination of water or air, etc. The majority of the COFs are made by the reversible imine chemistry, which lacks long term chemical stability under harsh conditions, which limits their stability. The present invention is based on a simple and robust reaction to transform the imine-based COFs into a fully conjugated COF without losing porosity and crystallinity. The method is general and can be applied to a wide range of COFs. Moreover, it is shown that the resulting materials have superior stability in the presence of triflic acid (one of the strongest organic acid), strong base, strong oxidant and reducing agents, which represent significant improvement to these pristine COFs before chemical transformation. Also, superhydrophobic materials can be obtained from such transformations.

The method results in a chemical transformation that endows a COF with exceptional chemical stability. Furthermore, the COF of the present invention are anticipated to have better semiconducting properties, which will make them better candidates for composite materials or for photocatalytic applications.

In some embodiments, the contacting step comprises introducing a COF comprising an imine group to a phenylacetylene, or vice versa, or mixing a COF comprising an imine group and a phenylacetylene. In some embodiments, the suitable reaction condition comprises a first organic solvent (such as BF$_3$.OEt$_2$, chloranil), toluene, or a mixture thereof). In some embodiments, the heating step comprises heating the mixture to a temperature at least about 60° C., about 70° C., about 80° C., about 90° C., about 100° C., or about 110° C., or within a range from about 60° C. to about 160° C., from about 70° C. to about 150° C., from about 80° C. to about 140° C., from about 90° C. to about 130° C., and from about 100° C. to about 120° C.).

In a particular embodiment, COFs, phenylacetylene, BF$_3$.OEt$_2$, chloranil, and of toluene are added to a vial. The vial is sealed and heated under N$_2$ at 110° C. in an oil bath. After 1-3 days, the mixture is cooled to room temperature and the precipitate is isolated via centrifugation. The reaction mixture is then washed with THF and optionally quenched with saturated aqueous sodium bicarbonate. Subsequently, the solids are washed with THF (such as for about 12 h) and dried (such as under vacuum).

The present invention provides for a covalent organic framework (COF) comprising a quinoline group. In some embodiments, the COF does not comprise any imine group. In some embodiments, the COF is a product of the method of the present invention. The present invention provides for a composition comprising: (a) a covalent organic framework (COF) comprising an imine group, and (b) a phenylacetylene.

COFs comprise a class of materials based on the atomically precise organization of organic subunits into 2- or 3-dimensional porous crystalline structures connected by strong covalent bonds with predictable control over composition, topology and porosity. Examples of COFs, and methods to produce them, are taught in the following: Diercks, et al. (2017), Science 355, eaal1585; Segura, et al. (2016), Chem. Soc. Rev. 45:5635-5671; Uribe-Romo, et al. (2009) J. Am. Chem. Soc. 131:4570-4571; and, U.S. Patent Application Publication Nos. 2018/0319821, 2018/0272313, 2017/0362190, 2017/0314737, 2017/0130349, 2016/0376282, 2015/0299147, 2015/0266885, 2014/0148596, 2014/0037944, 2011/0236301, 2010/0143693, and 2010/0043636 (all of which are hereby incorporated by reference in regards to the use and making of the COFs taught thereof). The COFs comprising an imine group can be any COF taught in the references above, or in this application herein, which comprise an imine group or have one or more imine groups added thereof.

In some embodiments, the phenylacetylene has the chemical structure:

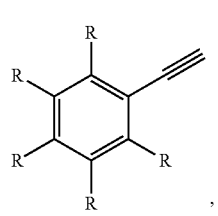

(I)

wherein each R is independently —H, —COOR1, —CHO, —X, —CN, - or R1, wherein each R1 is independently a straight or branched substituted or unsubstituted alkyl chain, and X is a halogen. In some embodiments, X is F, Br, or Cl. In some embodiments, R1 has up to about 20 or about 30 carbon atoms. In some embodiments, R1 has 1, 2, 3, 4, 5, 6, 7, 8, 9, or 10 carbon atoms. In some embodiments, the straight or branched alkyl chain is fully or partially substituted with one or more halogens. In some embodiments, R and/or R1 is —CH$_3$, —(CH$_2$)$_n$CH$_3$, —CH(CH$_3$)$_2$, or —C(CH$_3$)$_3$, wherein n is 1, 2, 3, 4, 5, 6, 7, 8, 9, or 10, or an integer up to about 20 or about 30, wherein one or more, or all, of the H are substituted with a X. In some embodiments, R and/or R1 is —COOCH$_3$, or —COO(CH$_2$)$_n$CH$_3$, wherein n is 1, 2, 3, 4, 5, 6, 7, 8, 9, or 10, or an integer up to about 20 or about 30. In some embodiments, R and/or R1 is —CX$_3$. In some embodiments, 1, 2, 3, 4, or 5 R's are —H. In some embodiments, the phenylacetylene comprises more than one R that is not —H, and all of these R's that are not —H are identical.

In some embodiments, the phenylacetylene has the chemical structure:

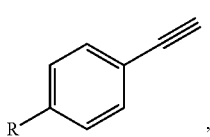

(Ia)

wherein R is as described for chemical structure (I). In some embodiments, the quinoline group has the chemical structure:

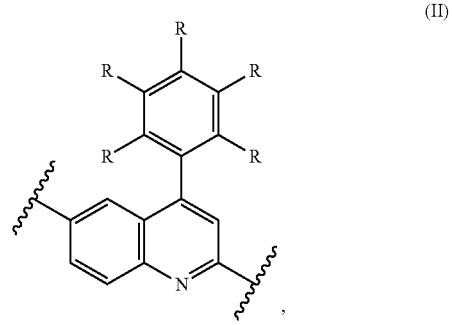

(II)

wherein R is as described for chemical structure (I). In some embodiments, 1, 2, 3, 4, or 5 R's are —H. In some embodiments, the quinoline group comprises more than one R that is not —H, and all of these R's that are not —H are identical.

In some embodiments, the quinoline group has the chemical structure:

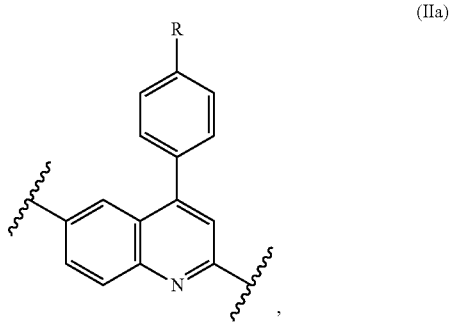

(IIa)

wherein R is as described for chemical structure (I).

In some embodiments, the superhydrophobic material is freestanding, or the superhydrophobic material is a surface coating on a substrate. In some embodiments, the substrate is selected from the group consisting of glass, metal, plastic, paper, wood, concrete and masonry. In some embodiments, the substrate is selected from the group consisting of a windshield, a glass plate, a metal plate, a metal object and a glove.

In some embodiments, a water droplet on a flat surface of the hydrophobic surface, or the exposed surface, has a water contact angle of equal to or more than about 90°, 100°, 110°, 120°, 130°, 140°, or 150°, or a range between any two values thereof. In some embodiments, a water droplet on a flat surface of the hydrophobic surface, or the exposed surface, has a water contact angle from about 125° to about 155°.

REFERENCES CITED

1. Diercks, C. S. & Yaghi, O. M. The atom, the molecule, and the covalent organic framework. Science 355, eaal1585 (2017).
2. Furukawa, H. & Yaghi, O. M. Storage of hydrogen, methane, and carbon dioxide in highly porous covalent organic frameworks for clean energy applications. J. Am. Chem. Soc. 131, 8875-8883 (2009).
3. Oh, H. et al. A cryogenically flexible covalent organic framework for efficient hydrogen isotope separation by quantum sieving. Angew. Chem. Int. Ed. 52, 13219-13222 (2013).
4. Ding, S.-Y. et al. Thioether-based fluorescent covalent organic framework for selective detection and facile removal of mercury (II). J. Am. Chem. Soc. 138, 3031-3037 (2016).
5. Lu, S. et al. Synthesis of ultrafine and highly dispersed metal nanoparticles confined in a thioether-containing covalent organic framework and their catalytic applications. J. Am. Chem. Soc. 139, 17082-17088 (2017).
6. Wan, S., Guo, J., Kim, J., Ihee, H. & Jiang, D. A belt-shaped, blue luminescent, and semiconducting covalent organic framework. Angew. Chem. Int. Ed. 120, 8958-8962 (2008).
7. DeBlase, C. R., Silberstein, K. E., Truong, T.-T., Abruña, H. D. & Dichtel, W. R. β-Ketoenamine-linked covalent organic frameworks capable of pseudocapacitive energy storage. J. Am. Chem. Soc. 135, 16821-16824 (2013).
8. Jin, Y., Hu, Y. & Zhang, W. Tessellated multiporous two-dimensional covalent organic frameworks. Nat. Rev. Chem. 1, 0056 (2017).
9. Huang, N. et al. Multiple-component covalent organic frameworks. Nat. Commun. 7, 12325 (2016).
10. Cote, A. P. et al. Porous, crystalline, covalent organic frameworks. Science 310, 1166-1170 (2005).
11. Cote, A. P., El-Kaderi, H. M., Furukawa, H., Hunt, J. R. & Yaghi, O. M. Reticular synthesis of microporous and mesoporous 2D covalent organic frameworks. J. Am. Chem. Soc. 129, 12914-12915 (2007).
12. Wan, S., Guo, J., Kim, J., Ihee, H. & Jiang, D. A photoconductive covalent organic framework: self-condensed arene cubes composed of eclipsed 2D polypyrene sheets for photocurrent generation. Angew. Chem. Int. Ed. 48, 5439-5442 (2009).
13. Segura, J. L., Mancherfo, M. J. & Zamora, F. Covalent organic frameworks based on Schiff-base chemistry: synthesis, properties and potential applications. Chem. Soc. Rev. 45, 5635-5671 (2016).
14. Qian, C. et al. Toward covalent organic frameworks bearing three different kinds of pores: the strategy for construction and COF-to-COF transformation via heterogeneous linker exchange. J. Am. Chem. Soc. 139, 6736-6743 (2017).
15. Kandambeth, S. et al. Construction of crystalline 2D covalent organic frameworks with remarkable chemical (acid/base) stability via a combined reversible and irreversible route. J. Am. Chem. Soc. 134, 19524-19527 (2012).
16. Kandambeth, S. et al. Enhancement of chemical stability and crystallinity in porphyrin-containing covalent organic frameworks by intramolecular hydrogen bonds. Angew. Chem. Int. Ed. 125, 13290-13294 (2013).
17. Chen, X. et al. Locking covalent organic frameworks with hydrogen bonds: general and remarkable effects on crystalline structure, physical properties, and photochemical activity. J. Am. Chem. Soc. 137, 3241-3247 (2015).
18. Wei, P.-F. et al. Benzoxazole-linked ultrastable covalent organic frameworks for photocatalysis. J. Am. Chem. Soc. 140, 4623-4631 (2018).
19. Arjun, H. et al. Ultrastable imine-based covalent organic frameworks for sulfuric acid recovery: an effect of interlayer hydrogen bonding. Angew. Chem. Int. Ed. 57, 5797-5802 (2018).
20. Xu, Y., Jin, S., Xu, H., Nagai, A. & Jiang, D. Conjugated microporous polymers: design, synthesis and application. Chem. Soc. Rev. 42, 8012-8031 (2013).
21. Rao, M. R., Fang, Y., De Feyter, S. & Perepichka, D. F. Conjugated covalent organic frameworks via michael addition-elimination. J. Am. Chem. Soc. 139, 2421-2427 (2017).
22. Liu, W. et al. A two-dimensional conjugated aromatic polymer via C—C coupling reaction. Nat. Chem. 9, 563 (2017).
23. Liu, J. et al. Solution synthesis of semiconducting two-dimensional polymer via trimerization of carbonitrile. J. Am. Chem. Soc. 139, 11666-11669 (2017).
24. Jin, E. et al. Two-dimensional $sp^2$ carbon-conjugated covalent organic frameworks. Science 357, 673-676 (2017).
25. Nagai, A. et al. Pore surface engineering in covalent organic frameworks. Nat. Commun. 2, 536 (2011).
26. Huang, N., Krishna, R. & Jiang, D. Tailor-made pore surface engineering in covalent organic frameworks: systematic functionalization for performance screening. J. Am. Chem. Soc. 137, 7079-7082 (2015).
27. Khayum, M. A. et al. Chemically delaminated free-standing ultrathin covalent organic nanosheets. Angew. Chem. Int. Ed. 55, 15604-15608 (2016).
28. Lohse, M. S. et al. Sequential pore wall modification in a covalent organic framework for application in lactic acid adsorption. Chem. Mater. 28, 626-631 (2016).
29. Waller, P. J. et al. Chemical conversion of linkages in covalent organic frameworks. J. Am. Chem. Soc. 138, 15519-15522 (2016).
30. Dibble, D. J. et al. An Aza-Diels-Alder route to polyquinolines. Macromolecules 48, 557-561 (2015).
31. Xu, H., Gao, J. & Jiang, D. Stable, crystalline, porous, covalent organic frameworks as a platform for chiral organocatalysts. Nat. Chem. 7, 905 (2015).
32. Hu, Y. et al. Probing the chemical structure of monolayer covalent-organic frameworks grown via Schiff-base condensation reactions. ChemComm 52, 9941-9944 (2016).
33. Gammon, W., Kraft, O., Reilly, A. & Holloway, B. Experimental comparison of N (is) X-ray photoelectron spectroscopy binding energies of hard and elastic amorphous carbon nitride films with reference organic compounds. Carbon N. Y. 41, 1917-1923 (2003).
34. Zhu, Y. et al. Unravelling surface and interfacial structures of a metal-organic framework by transmission electron microscopy. Nat. Mater. 16, 532-536 (2017).
35. Medina, D. D. et al. Oriented thin films of a benzodithiophene covalent organic framework. ACS Nano 8, 4042-4052 (2014).
36. Ascherl, L. et al. Molecular docking sites designed for the generation of highly crystalline covalent organic frameworks. Nat. Chem. 8, 310-316 (2016).
37. Peng, Y. et al. Ultrathin two-dimensional covalent organic framework nanosheets: preparation and application in highly sensitive and selective DNA detection. J. Am. Chem. Soc. 139, 8698-8704 (2017).
38. Bai, L. et al. Nanoscale covalent organic frameworks as smart carriers for drug delivery. ChemComm 52, 4128-4131 (2016).
39. Mullangi, D., Shalini, S., Nandi, S., Choksi, B. & Vaidhyanathan, R. Superhydrophobic covalent organic frameworks for chemical resistant coatings and hydrophobic paper and textile composites. J. Mater. Chem. A 5, 8376-8384 (2017).
40. Zhang, W., Hu, Y., Ge, J., Jiang, H.-L. & Yu, S.-H. A facile and general coating approach to moisture/water- 41. Nguyen, J. G. & Cohen, S. M. Moisture-resistant and superhydrophobic metal-organic frameworks obtained via postsynthetic modification. J. Am. Chem. Soc. 132, 4560-4561 (2010).

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

Example 1

Facile Transformation of Imine Covalent Organic Frameworks into Ultrastable Crystalline Porous Aromatic Frameworks The growing interest in two-dimensional imine-based covalent organic frameworks (COFs) is inspired by their crystalline porous structures and the potential for extensive π-electron delocalization. The intrinsic reversibility and strong polarization of imine linkages, however, leads to insufficient chemical stability and optoelectronic properties. Developing COFs with improved robustness and π-delocalization is highly desirable but remains an unsettled challenge. Herein is described a facile strategy that transforms imine-linked COFs into ultrastable porous aromatic frameworks by kinetically fixing the reversible imine linkage via an aza-Diels-Alder cycloaddition reaction. The as-formed, quinoline-linked COFs not only retain crystallinity and porosity, but also display dramatically enhanced chemical stability over their imine-based COF precursors, rendering them among the most robust COFs up-to-date that can withstand strong acidic, basic and redox environment. Owing to the chemical diversity of the cycloaddition reaction and structural tunability of COFs, the pores of COFs can be readily engineered to realize pre-designed surface functionality.

Herein, a strategy is explored that can transform the dynamic imine linkages in COFs into more robust and conductive bonds while preserving the topology, crystallinity, and porosity of COFs. Starting from an imine COF can bypass the crystallization problem encountered in irreversible crosslinking, while the linkage transformation can significantly boost the chemical stability and electron delocalization in the resultant COFs. A number of COFs have been modified postsynthetically[25,26,27,28] to give functionally diverse and topologically identical porous materials. The modification reaction happens almost exclusively on the linkers that bear chemically addressable pendant groups, with only one exception in which the reaction targets the imine linkages to transform them into more stable amide linkages[29]. Herein is described a more versatile approach to kinetically fix the reversible linkage in imine COFs to afford crystalline and chemically robust porous 2D aromatic framework with extended π-electron delocalization (FIG. 1A). Thanks to the efficient Povarov (aza-Diels-Alder, aza-DA) reaction[30] between aryl imines and arylalkynes, the imine linkages in 2D COFs can be converted to yield the corresponding quinoline-linked COFs (denoted as MF-1a-e). Owing to the structural tunability of starting imine-linked COFs and substrate diversity of the aza-DA reaction, a large variety of functional moieties can be introduced to selectively alter the pore surface and wettability of the resultant COFs.

RESULTS AND DISCUSSION

Synthesis of the MFs Via Aza-DA Reaction

The viability of the Povarov reaction was first demonstrated on a prototype imine-linked COF, a highly crystalline and porous COF denoted as COF-1[31]. COF-1 is readily obtained following a reported protocol and is subjected to the reaction with phenylacetylene (1a) at 110° C. in the presence of $BF_3.Et_2O$ (1.5 equiv. per imine functionality) and chloranil in toluene for 72 h. The solid separated from the reaction mixture is washed with excess anhydrous THF and saturated $NaHCO_3$, and then dried under vacuum to afford MF-1a as dark yellow solid.

Characterizations of the MFs

Figure 2A:
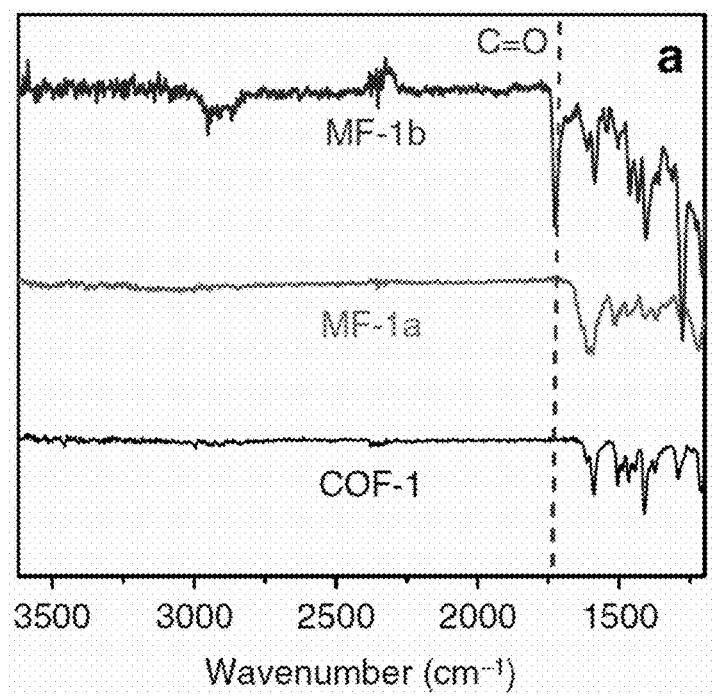
FIG. 2A. Characterization of original COF-1 (black) and post-synthetically modified MF-1a (red) and MF-1b (blue). FT-IR spectra.
Figure 2B:
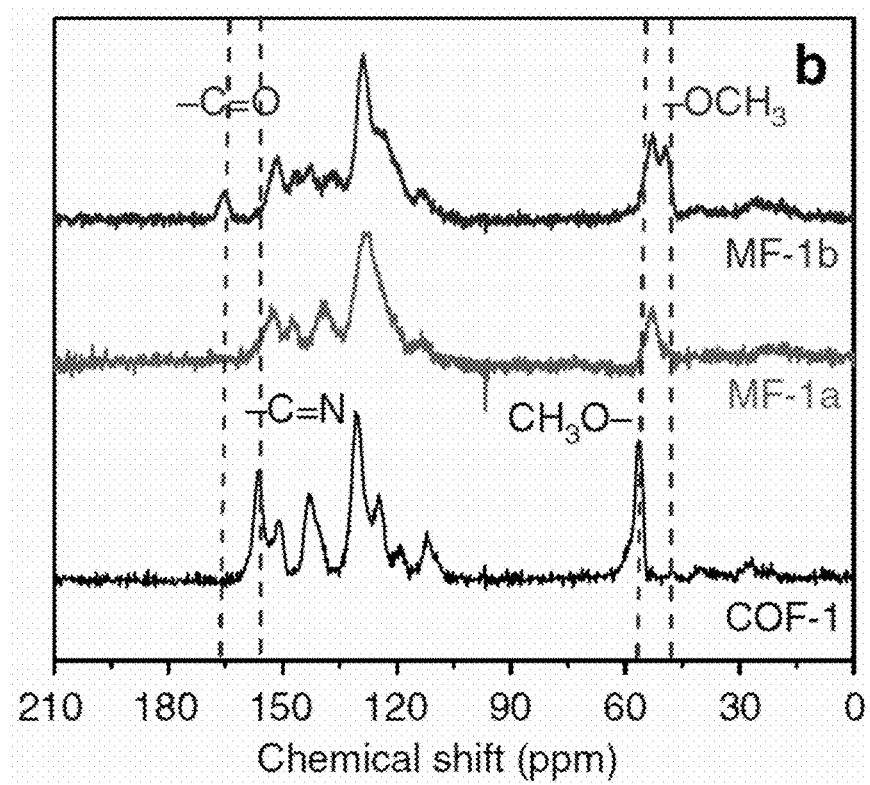
FIG. 2B. Characterization of original COF-1 (black) and post-synthetically modified MF-1a (red) and MF-1b (blue). Solid-state $^{13}$C CP-MAS NMR spectra.

The successful addition of phenylacetylene onto COF-1 is verified by several analytical methods. Comparison of the Fourier-transform infrared (FT-IR) spectra of MF-1a and COF-1 (FIG. 2A) reveals a new cluster of peaks at ~1600 $cm^{-1}$ that correspond to the stretch of aromatic quinoline core[30] and blue shift of the C—C=N—C stretch (from 1202 to 1222 $cm^{-1}$) after the reaction. As a control, the 1D imine-polymer is subjected to Povarov reaction to afford modified quinoline-linked polymer, which revealed a similar cluster of peaks at ~1600 $cm^{-1}$ arising from the aromatic quinoline core and blue shift of the C—C=N—C stretch (from 1207 to 1214 $cm^{-1}$). Moreover, the C—C=N—C stretching is close to the model compound, diphenyl quinoline (1238 $cm^{-1}$). Another control experiment run under the identical reaction conditions except without phenylacetylene 1a confirmed that the Lewis acid catalyst ($BF_3.Et_2O$) and chloranil alone induced no chemical modification of COF-1, as revealed by the lack of evident changes in the FT-IR spectra of COF-1. Given that the quinoline vibration at ~1622 $cm^{-1}$ in the spectrum of MF-1a overlaps with C=N imine stretch of COF-1, 1a is replaced with a para-ester substituted phenylacetylene derivative (1b) to afford MF-1b bearing a characteristic chemical probe. FT-IR spectra of MF-1b reveals a peak at ~1725 $cm^{-1}$, arising from the carbonyl moiety (FIG. 2A), which is also different from that in the spectra of free 1b (~1702 $cm^{-1}$). Solid-state $^{13}C$ cross polarization magic angle spinning (CP-MAS) NMR spectroscopy reveals an apparent up-field shift of the aromatic and —OMe resonances in the spectrum of MF-1a compared to that of COF-1. Such up-field shift is again observed in the spectra of MF-1b, together with two well-resolved but characteristic peaks at 165 and 50 ppm that could be assigned to the methyl ester groups (FIG. 2B). These spectroscopic changes corroborate well with successful conversion of the imine linkages of the COF framework following the Povarov cycloaddition.

Figure 1B:
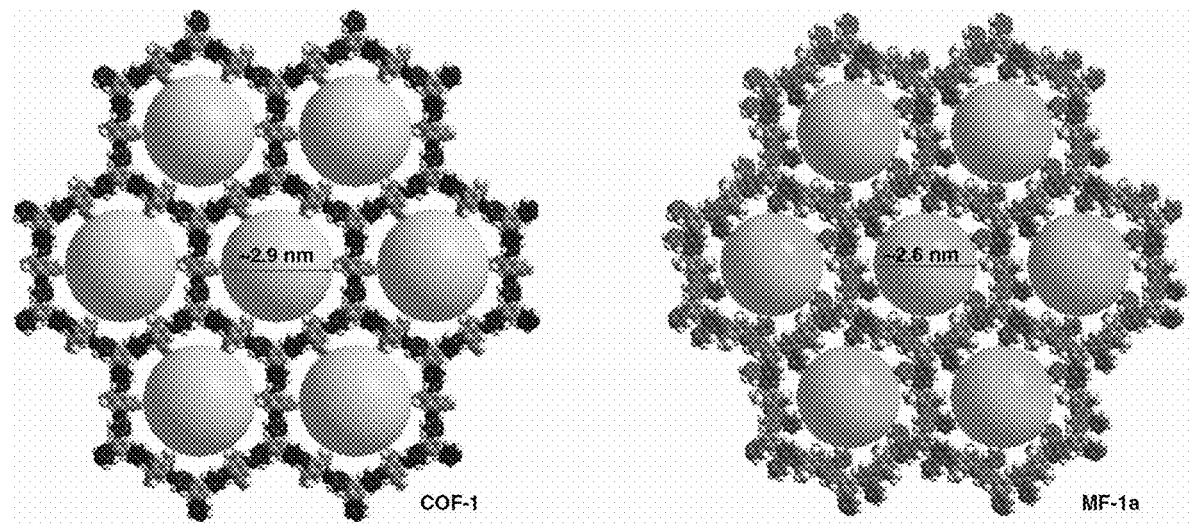
FIG. 1B. The simulated modeled structure showing the extended frameworks of COF-1 and MF-1a. The yellow and cyan sphere indicate pore diameter of ~2.9 and ~2.6 nm. Note that the illustrated structure of MF-1 contains fully converted quinolines and does not represent the actual degree of transformation.
Figure 2C:
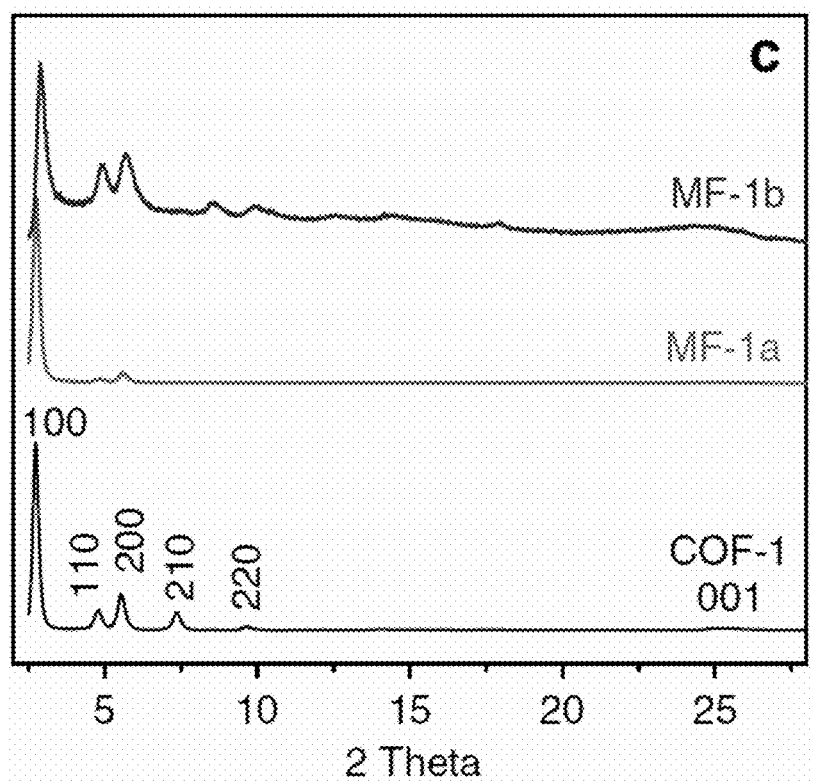
FIG. 2C. Characterization of original COF-1 (black) and post-synthetically modified MF-1a (red) and MF-1b (blue). PXRD patterns showing retention of crystallinity after the Povarov reaction.

The powder X-ray diffraction (PXRD) pattern of COF-1 exhibits six prominent diffraction peaks, with the most intensive one at 2.73° and the five other peaks at 4.790, 5.54°, 7.35°, 9.65°, and 25.20, assigned to the (100), (110), (200), (210), (220), and (001) facets, respectively (FIG. 2C, black curve). After modification, the PXRD pattern of MF-1a exhibits four prominent diffraction peaks, with the most intensive one at 2.75° and the three other peaks at 4.82°, 5.58°, and 25.1°, corresponding to the (100), (110), (200), and (001) facets, respectively (FIG. 2C, red curve). The (100) peaks of MF-1a and MF-1b have a small full-width at half-maximum (FWHM) values of 0.25° and 0.290, respectively, suggesting their high crystallinity. Such peaks show insignificant shift compared to that of COF-1 (FWHM=0.240) (FIG. 2C), indicating preservation of the crystalline framework during the linkage transformation. Using an optimized monolayer structure, AA and staggered AB stacking modes are generated and optimized. The simulated PXRD pattern of the modeled 2D frameworks in AA stacking mode is in good agreement with the experimental peak positions. The PXRD pattern of MF-1a and MF-1b demonstrates similar high crystallinity and insignificant shift of (100) and (001) peaks as compared with that of COF-1 (FIG. 2C), indicating the preservation of the crystalline framework during the linkage transformation. Such patterns also match with the simulated PXRD pattern of the modeled 2D frameworks in AA stacking mode (FIG. 1B). Pawley refinement shows the negligible difference between the simulated XRD and experimental patterns, while the staggered AB stacking mode do not reproduce the experimental profile. UV-Vis diffuse reflectance spectra of MF-1a shows a red shift as compared with COF-1, which is indicative of enhanced a delocalization. Upon modification, MF-1a shows a reduced optical bandgap of 2.30 eV compared to that of COF-1 (2.52 eV). As shown by thermogravimetric analysis, MF-1a has a slightly higher decomposition onset temperature compared to COF-1. In addition, it displays less weight loss than COF-1 after incubation at 400° C., indicating better thermal stability after the chemical transformation.

Figure 2D:
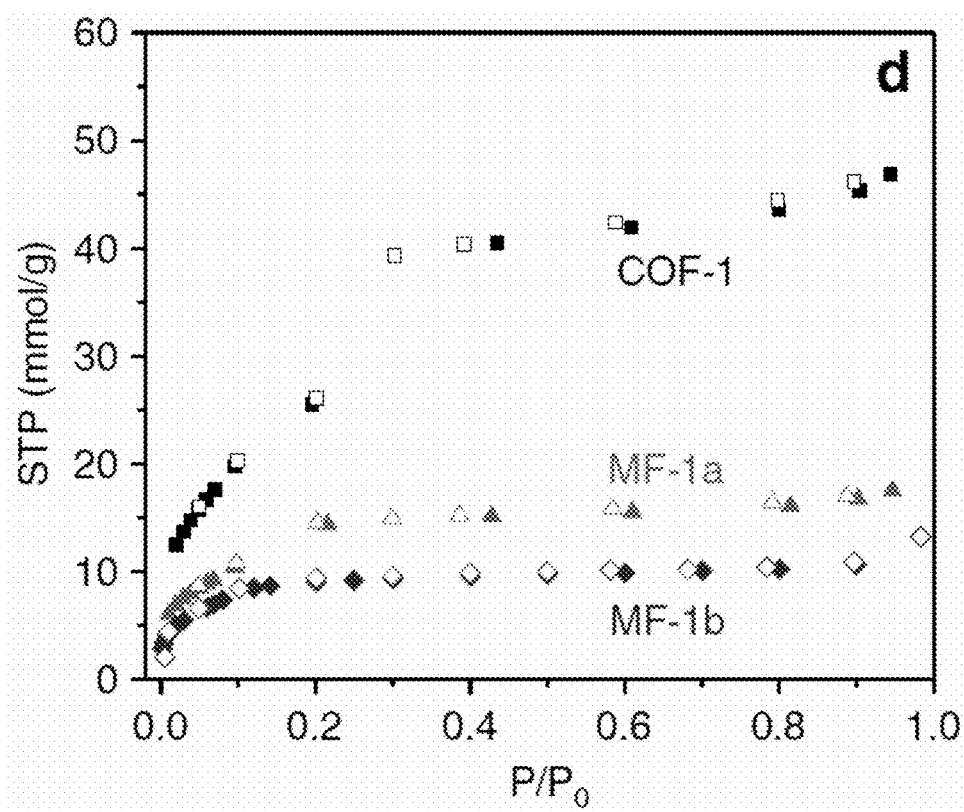
FIG. 2D. Characterization of original COF-1 (black) and post-synthetically modified MF-1a (red) and MF-1b (blue). $N_2$ sorption isotherm curves.

$N_2$ sorption analyses performed at 77 K reveals a Brunauer-Emmett-Teller (BET) surface area of 1760, 955, and 590 $m^2 g^{-1}$ for COF-1, MF-1a, and MF-1b, respectively (FIG. 2D). The decrease of surface area corroborates with the increased framework mass and reduction of the pore volume. The type IV isotherms of MF-1a, MF-1b, and COF-1 are not only indicative of the mesoporous characters, but also suggest that the chemical modification does not lead to significant changes in the framework structure. Pore size distribution analysis indicates a pore size reduction from 3.0 to 2.1 nm upon chemical transformation. Additional SEM studies shows that the morphology of MF-1a is similar to that of the pristine COF-1. X-ray photoelectron spectroscopy (XPS) analyses are performed to provide more insight into the conversion from imine to quinoline. The N1s peak at ~398.0 eV in COF-1 can be attributed to the imine N atoms[32]. Upon modification, a fraction of the N1s core level is shifted to higher binding energies (~399.5 eV), corresponding to the C=N in quinoline moieties[33]. Based on the integration of the peak areas, the degrees of functionalization in MF-1a and MF-1b are assessed to be 27% and 25%, respectively. Further XPS depth profiling analysis indicates that the quinoline/imine nitrogen ratio remains constant after repeated exposure to high energy argon ion beam irradiations, confirming a uniform material composition from the surface to the buried body of the bulk. In the case of MF-1a, increasing the reaction time to 1 week results in a slight increase of the conversion to 29%, while increasing the concentration of all the reactants except COF-1 by 3-fold augments the conversion to 35%, suggesting that higher conversion may be achieved by further optimization of the reaction conditions.

Figure 3A:
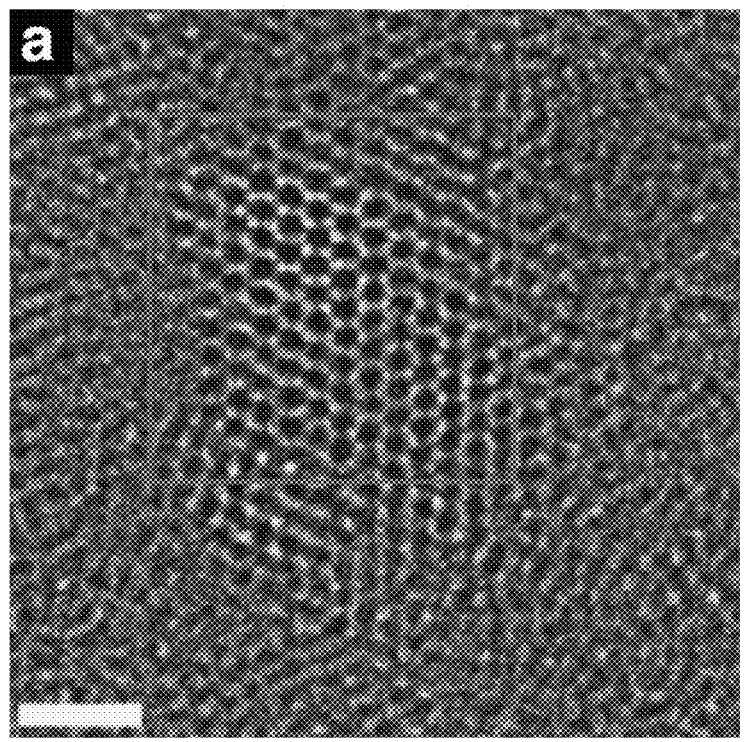
FIG. 3A. HRTEM characterization of COF-1 and MF-1a. Low-dose, high-resolution TEM image of COF-1 (scale bar, 10 nm).
Figure 3B:
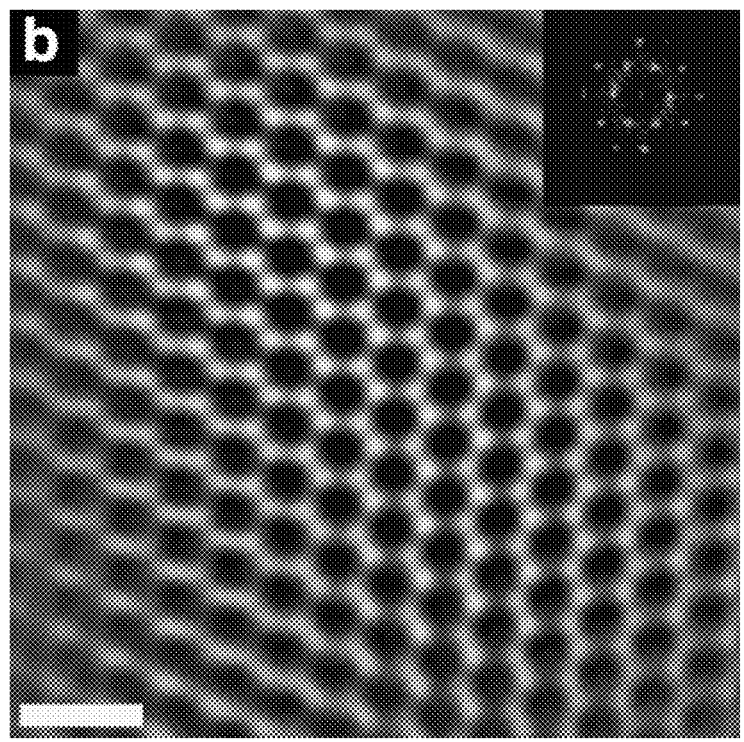
FIG. 3B. HRTEM characterization of COF-1 and MF-1a. The Fourier-filtered image of selected red square areas (scale bar, 5 nm), Inset: Fast Fourier Transform (FFT) from the red square on the COF-1.
Figure 3C:
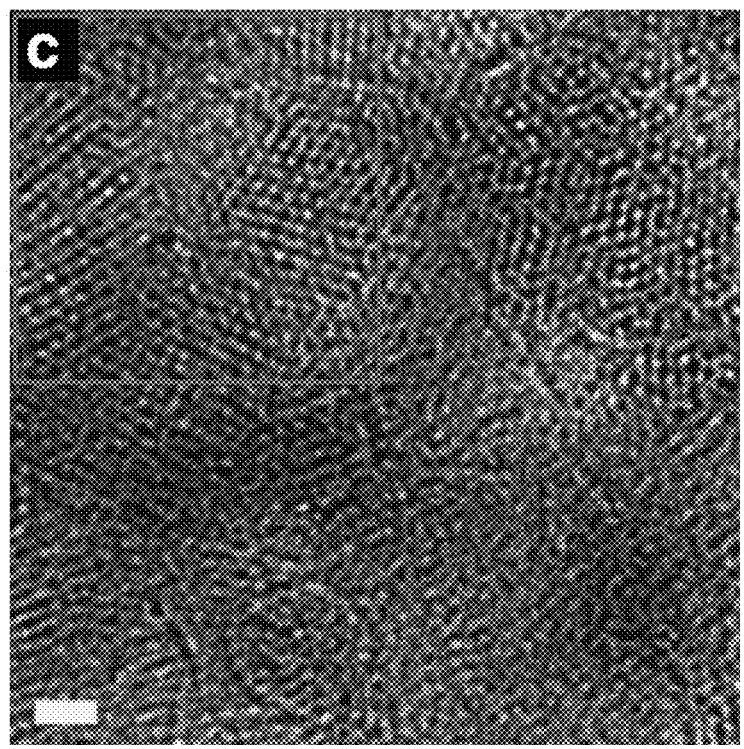
FIG. 3C. HRTEM characterization of COF-1 and MF-1a. Low-dose, high-resolution TEM image of MF-1a (scale bar, 10 nm).
Figure 3D:
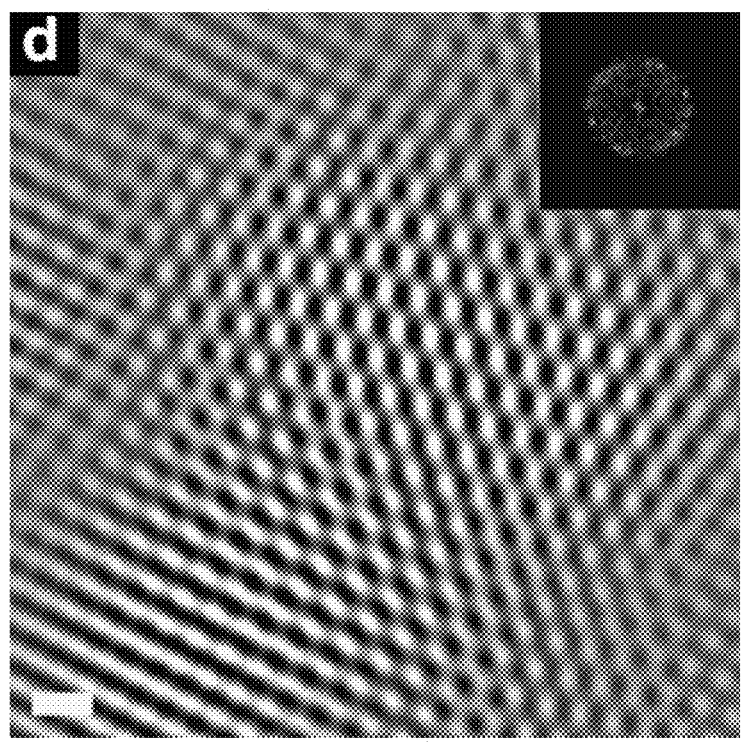

The periodic framework structural features of COF-1 and MF-1a are visualized by high-resolution transmission electron microscopy (HRTEM), using the low-dose TEM technique equipped with Gatan K2 Summit direct-detection electron-counting cameras and geometric/chromatic image aberration correction. The total electron dose is 2.1 e $Å^{-2}$ and the pixel size 0.72 Å. As shown in FIG. 3A, the honeycomb-like porous structure of COF-1 is clearly observed along the [111] direction, with the pore opening determined as 3.0±0.2 nm. Based on the Fourier-filtered image of a selected area (red square in FIG. 3A), one can clearly observe a hexagonal projected symmetry constructed by six white diffraction spots. Upon modification, MF-1a shows a decreased pore opening of 2.3±0.2 nm (FIG. 3C) with the preservation of similar honeycomb-like porous structure (FIGS. 3B and 3D). The direct observation of the pore opening decrease in the framework structures before and after modification, which is consistent with the modeled structures as shown in FIG. 1B and pore size distributions, confirms the effectiveness of the framework-to-framework transformation. Note that COF samples are highly electron-beam sensitive, making the acquisition of high-resolution extremely challenging[35,36,37], this represents a rare example in which the individual building units of COFs are directly and clearly observed by HRTEM.

Chemical Stability

Figure 4A:
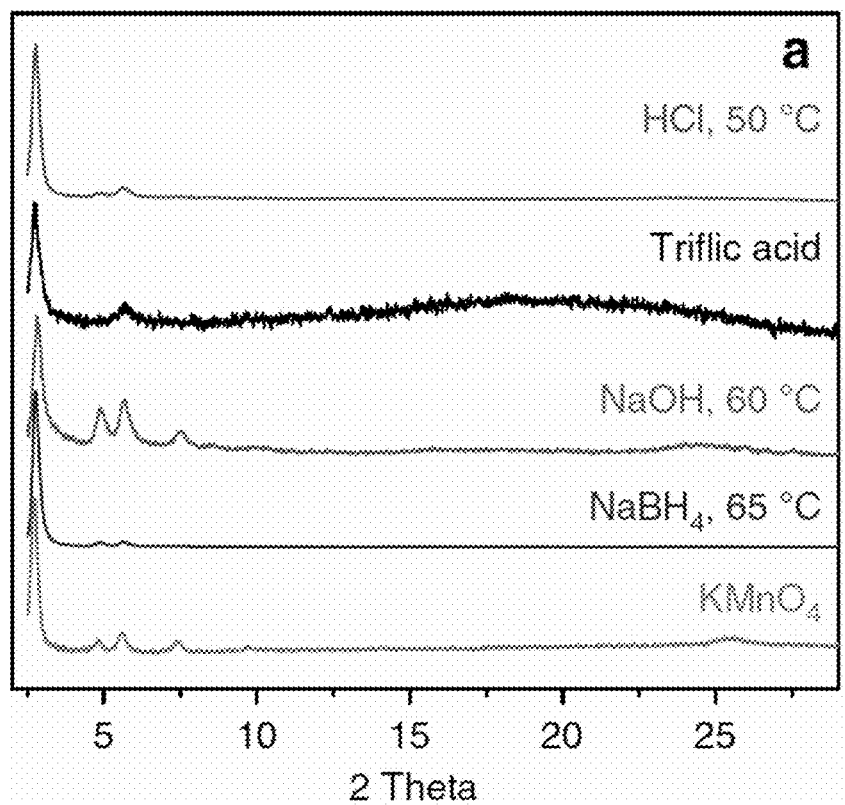
FIG. 4A. Chemical stability of MF-1a and COF-1. PXRD patterns of MF-1a after treatment with 12 M HCl at 50° C. for 8 h (green), 98% triflic acid at ambient temperature for 3 days (black), 14 M NaOH in $H_2O$/MeOH solution at 60° C. for 1 day (red), 5 equiv. of $NaBH_4$ in MeOH at 65° C. for 1 day (blue), and 5 equiv. of $KMnO_4$ in $H_2O/CH_3CN$ solution at ambient temperature for 1 day (purple).
Figure 4B:
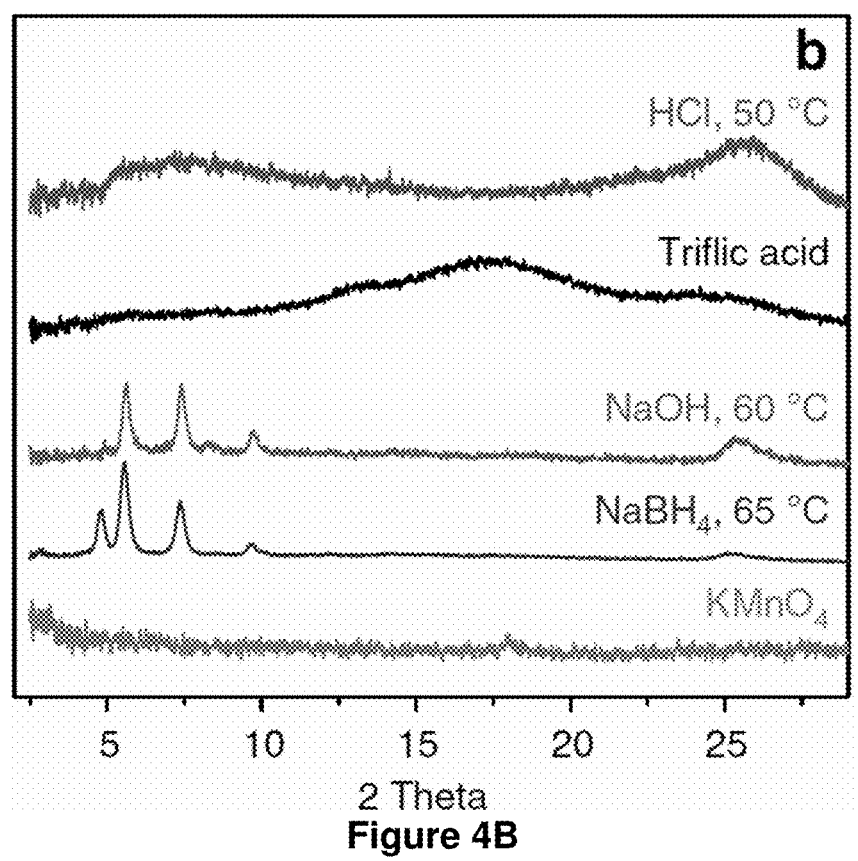
FIG. 4B. Chemical stability of MF-1a and COF-1. PXRD patterns of COF-1 after treatment with 12 M HCl at 50° C. for 8 h (green), 98% triflic acid at ambient temperature for 3 days (black), 14 M NaOH in H$_2$O/MeOH solution at 60° C. for 1 day (red), 5 equiv. of NaBH$_4$ in MeOH at 65° C. for 1 day (blue), and 5 equiv. of KMnO$_4$ in H$_2$O/CH$_3$CN solution at ambient temperature for 1 day (purple).

To assess the chemical stability of the modified framework structure, MF-1a is subjected to a variety of extremely harsh chemical conditions. The post-synthetically modified COF exhibits strikingly high chemical stability in strong mineral acid (12 M HCl at 50° C. for 8 h), superacid (98% TfOH, 3 days), strong base (14 M NaOH in $H_2O$/MeOH at 60° C., 1 day), strong oxidant ($KMnO_4$ in $H_2O$/$CH_3CN$ solution, 1 day) and reducing agents ($NaBH_4$ in MeOH at 65° C., 1 day), as revealed by the retention of major diffraction peaks in the PXRD patterns of the treated samples (FIG. 4A). Remarkably, MF-1a retains its crystallinity after being exposed to 12 M HCl at room temperature for 2 months, or to boiling acids (1 M and 12 M HCl) and bases (1 M and 14 M NaOH) for 1 day. IR spectra of the acid-treated MF-1a indicates the appearance of aldehyde vibration band at ~1670 $cm^{-1}$, suggesting partial hydrolysis of the remaining imine bonds under such forcing conditions. As the porous framework is well preserved due to the introduced quinoline linkage, the hydrolysis conceivably gives a patchy framework that is decorated with dangling aldehyde and amine functional groups, which present further opportunities for introducing extra functionality. Such a high framework stability compares favorably to other known stable framework materials. In sharp contrast, the corresponding COF-1, one of the most chemically robust imine COFs reported up-to-date, is rendered amorphous or loses framework periodicity (FIG. 4B). The residual weight percentages of MF-1a under the conditions of strong acid (12 M HCl at 50° C.) and strong base (14 M NaOH at 60° C.) are 88 and 83 wt % while the pristine COF-1 exhibit more significant weight loss after acid/base treatment. Moreover, MF-1a still remains porous with only 5-25% decrease in surface area, whereas the pristine COF-1 displays much more significant loss (80-100%) in surface area. The vast differential in the stability of the MF-1 library relative to COF-1 clearly underscores the significance of transforming dynamic imines to much more robust quinoline units. The greatly enhanced stability towards chemical oxidation and reduction is particularly remarkable and is relevant for practical applications involving redox processes.

Generality of the Povarov Addition Approach

Figure 5A:
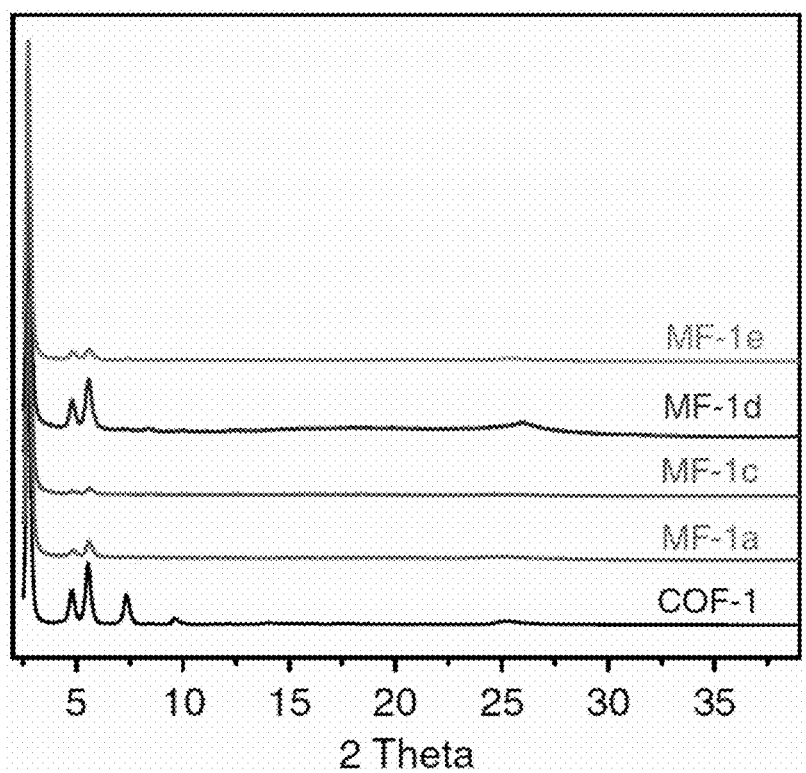
FIG. 5A. Structural characterization and surface properties of MF-1 series. Powder XRD patterns of COF-1 (black), MF-1a (red), MF-1c (green), MF-1d (blue), and MF-1e (purple).
Figure 5B:
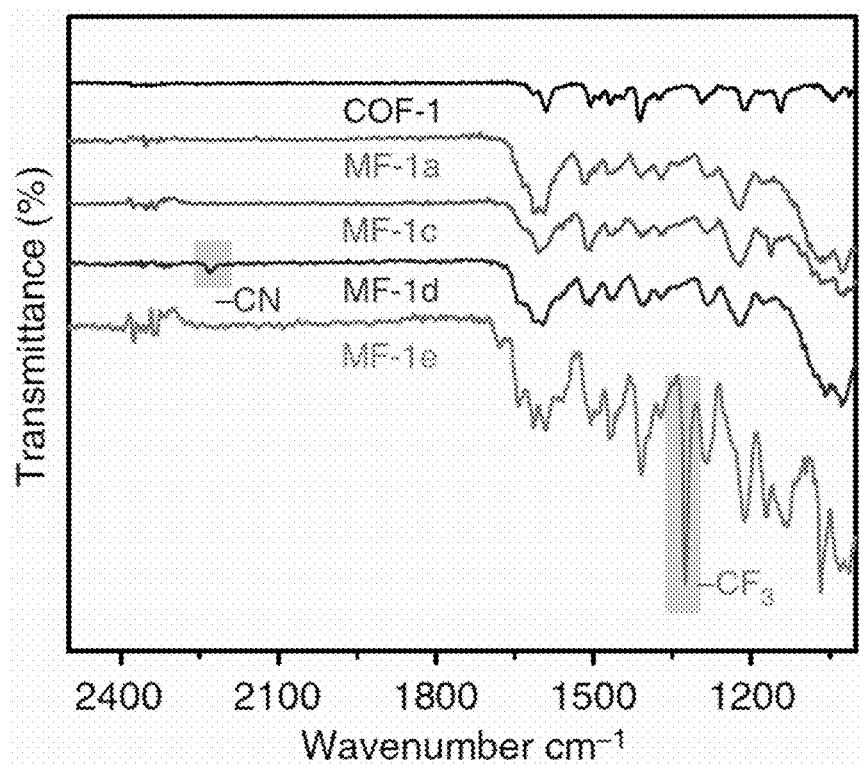
FIG. 5B. Structural characterization and surface properties of MF-1 series. FT-IR spectra of COF-1 and MF-1a, c-e. The peaks highlighted in cyan are characteristic vibrations from these functional groups.

The cycloaddition-based approach allows the integration of various functionalities onto the pores of COFs from substituted arylalkynes, thus rendering it much more versatile than the oxidation-based post-synthetic modification of imine-COFs[29], and click reaction-based post-synthetic modification of COFs, which requires specifically designed azide/ethynyl-appended building blocks and metal catalyst (e.g., CuI)[25,26]. The generality is demonstrated by reacting COF-1 with para-substituted arylalkynes 1c-e under similar reaction conditions to give MF-1c-e bearing fluorine, nitrile and trifluoromethyl groups on the pore surfaces. The PXRD analysis confirmed the retention of crystallinity after the Povarov reaction (FIG. 5A) while solid-state CP-MAS $^{13}$C NMR and FT-IR spectroscopy reveals changes that correspond to the conversion of imine bonds to quinoline C=N bonds (FIG. 5B). Notably, the characteristic —CN vibrational peak (~2231 cm$^{-1}$) and —CF$_3$ stretch (~1325 cm$^{-1}$) in the FT-IR spectra of MF-1b and MF-1c, which are different from these in the spectra of free 1d (2226 cm$^{-1}$) and 1e (1320 cm$^{-1}$), together with the absence of alkyne peaks (~3200-3300 cm$^{-1}$ for —C≡C—H stretch and ~2100 cm$^{-1}$ for —C≡C-stretch), unambiguously confirm the chemical attachment of —PhCN and —PhCF$_3$ groups to the framework (highlighted in cyan in FIG. 5B) that was concomitant with successful Povarov reaction. XPS analysis shows the degree of functionalization for MF-1 c-e is 27%, 29%, and 26%, respectively, very similar to that of MF-1a-b.

Figure 6:
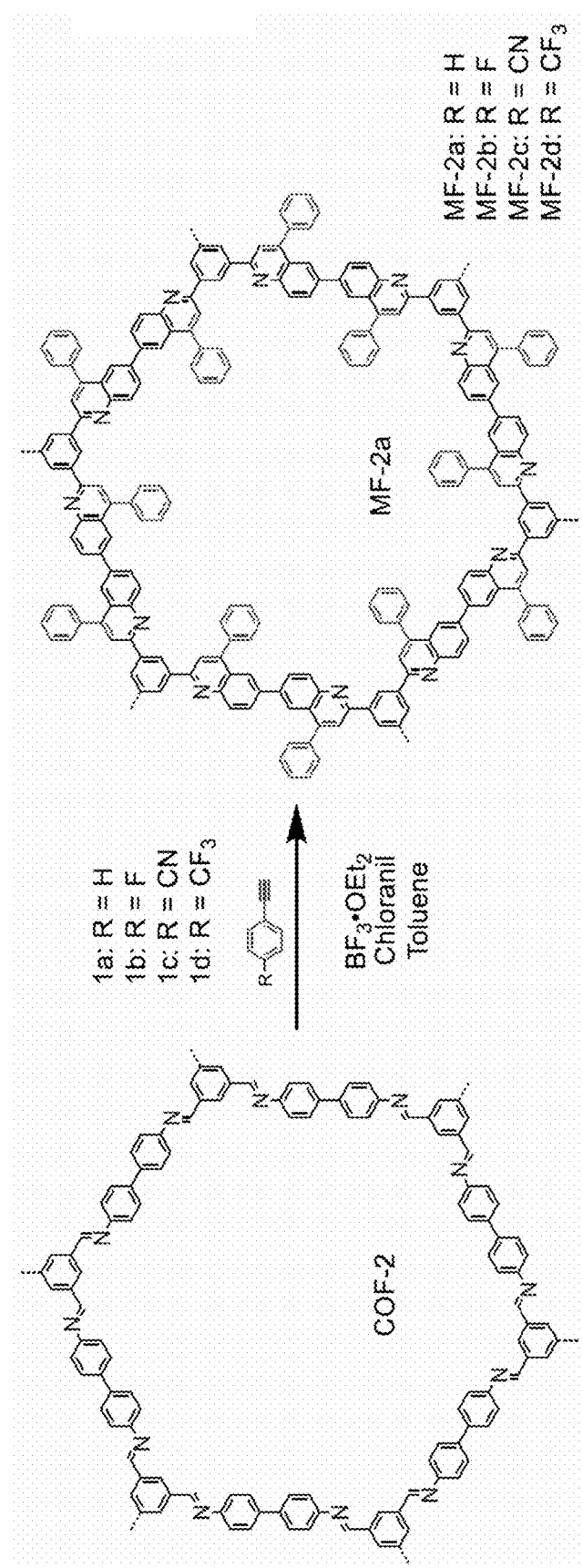
FIG. 6. Post-synthetic modification of COF-2 via aza-DA reaction. The reaction of COF-2 to give MF-2a-d.
Figure 7:
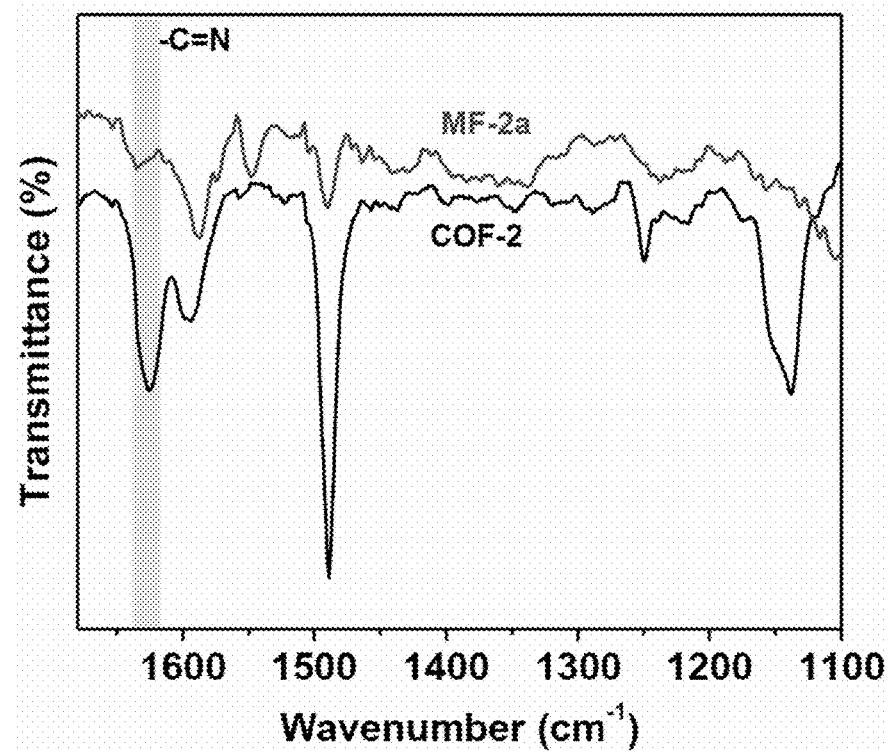
FIG. 7. FT-IR spectra of COF-2(black) and MF-2a (red).

This post-synthetic modification protocol can be applied to other imine-COFs as well, as demonstrated in the reaction with COF-2 (FIG. 6), which is readily synthesized following a routine solvothermal procedure[38]. The disappearance of the characteristic imine stretch at 1625 cm$^{-1}$ is clearly discernible in the FT-IR spectra of MF-2a (FIG. 7). The retention of morphology, crystallinity, and porosity in MF-2a is confirmed by SEM images, PXRD analysis and N$_2$ sorption analysis, respectively. The enhanced chemical stability is demonstrated by treating MF-2a with a strong acid (12 M HCl, 1 day), the PXRD of which remain unchanged while COF-2 decomposes completely under the same conditions. Finally, a variety of organic functionalities such as —F, —CN, and —CF$_3$ groups have been successfully incorporated into the porous crystalline framework via the Povarov reaction of COF-2, as verified by PXRD and FT-IR analyses. XPS analysis indicates the degree of functionalization in MF-2 a-d is 21%, 29%, 24%, and 29%, respectively, which is comparable to the MF-1 series. All these results correlate well with a successful chemical transformation of imine-COFs into more stable crystalline porous frameworks.

Customizable Surface Wettability

Figure 5C:
FIG. 5C. Structural characterization and surface properties of MF-1 series. Water contact angles (CA) of water droplet on the pressed pellet of COF-1 and MF-1a-e. MF-1b' is the NaHCO$_3$-treated MF-1b that undergoes partial ester hydrolysis.
Figure 8:
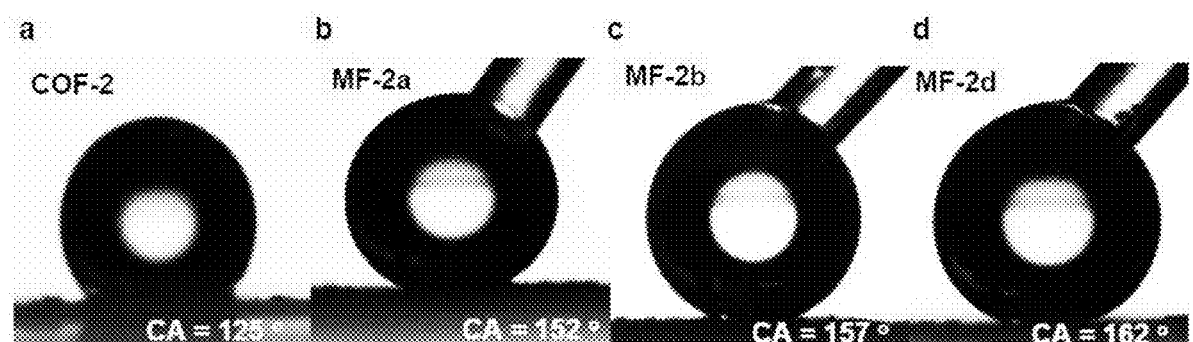
FIG. 8. Contact angle images of a water droplet on (a) COF-2, (b) MF-2a, (c) MF-2b, (d) MF-2d showing an increasing hydrophobicity when altering the fluorinated functionalities in MF-2.

The customizable surface functionality of stable COFs provides a convenient way to fabricate porous materials with controlled wettability, which has garnered continuous attention from both academia and industry[39,40,41]. The surface wettability of COFs before and after the Povarov reaction differs drastically and shows a strong dependence on both the COF structure and the substituent groups on the phenylacetylene. FIG. 5C shows water contact angles on the surface of COF-1 and MF-1a-e. The contact angle on MF-1a is ~125° while COF-1 exhibits a contact angle of only ~75°, indicating that the covalent modification of COFs significantly enhanced the hydrophobicity of the material. This increase in hydrophobicity is presumably due to the introduction of more hydrophobic aromatic rings onto the pore surfaces and decreased polarization after incorporating the imine bonds into the aromatic quinoline ring systems. Notably, incremental changes of contact angles are observed when altering the functional groups from —H (MF-1a, 1250) to —CN (MF-1d, 1320), —F (MF-1c, 1440), and —CF$_3$ (MF-1e, 1550), highlighting an effective way to systematically fine-tune COF surface wettability into the superhydrophobic region. The methyl ester-bearing MF-1b has a similar contact angle of 122°. Upon treatment with NaHCO$_3$, the contact angle (MF-1b') decreases significantly to 350, indicating the feasibility of imparting hydrophilicity via hydrolysis of ester moieties. Similar fine modulation of hydrophobicity is also observed in the series of MF-2s. MF-2a has a contact angle of 152° which is significantly higher than the 125° contact angle of the pristine COF-2 and the introduction of fluorinated functional groups (—F, and —CF$_3$) led to gradually increased hydrophobicity, evidenced by the contact angle change from —H (MF-2a, 1520) to —F (MF-2c, 157°) and —CF$_3$ (MF-2e, 1620) (FIG. 8).

A facile approach to deriving crystalline porous aromatic frameworks from readily available imine-COFs is developed by transforming the dynamic imine linkages into more stable quinoline aromatic ring systems via aza-Diels-Alder cycloaddition. The kinetic fixation of the imine linkages, even with only around 20-30% conversion, results in dramatically enhanced framework stability towards strong acid, base, and redox reagents. This framework-to-framework transformation offers a simple solution to the intrinsic instability associated with imine-COFs while retaining the framework's crystallinity and permanent porosity, while simultaneously enabling the tuning of pore surface functionalities and x electron delocalization. This succinct protocol paves the way to the synthesis of crystalline, porous aromatic frameworks that are difficult to obtain de novo, and it facilitate practical applications of organic framework materials that require enhanced chemical stability, semiconducting properties, and pore surface functionality.

Methods

Reagents

Acetone, acetonitrile, chloroform, dichloromethane, methanol, tetrahydrofuran (THF), toluene, and 1,4-dioxane are purchased from Fisher chemicals. 1-ethynyl-4-fluorobenzene and 1,3,5-tri-(4-aminophenyl)benzene are purchased from TCI. 1-ethynyl-4-(trifluoromethyl)benzene is purchased from 1Click Chemistry Stock Products. Methyl 4-ethynyl benzoate is purchased from AK scientific. 2,5-Dimethoxyterephthalaldehyde are purchased from Carbosynth chemicals. 2,4-diphenyl-quinoline are purchased from EnamineStore. Phenylacetylene, 4-ethynyl benzonitrile, boron trifluoride diethyl etherate, triethylamine are purchased from Alfa Aesar chemicals. Chloranil, triflic acid, 1,3,5-triformylbenzene, benzidine, mesitylene, o-dichlorobenzene, n-butanol are purchased from Sigma Aldrich chemicals.

Instrumentation and Characterization

Fourier transform infrared (FT-IR) spectra are recorded on a Perkin Elmer Spectrum One FT-IR system. Powder X-ray diffraction (PXRD) patterns are recorded on a Bruker Discovery D8 X-ray diffractometer and Rigaku MiniFLex 6G Benchtop XRD with Cu Kal radiation (λ=1.5406 Å). Nitrogen sorption isotherms are obtained at 77 K with a Micromeritics Instrument Corporation model 3Flex surface characterization analyzer. The Brunauer-Emmett-Teller (BET) method is utilized to calculate the specific surface areas. By using the non-local density functional theory (NLDFT) model, the pore size distribution is derived from the sorption curve. TGA measurements are performed on a TA Instruments Q5000IR TGA under Argon, by heating to 600° C. at a rate of 10° C. min$^{-1}$. Solid-state $^{13}$C CP-MAS NMR spectra are recorded on a BrukerAvance500 I (MF-1d sample only) and BrukerAvance500 II. The UV-vis diffuse reflectance measurement is performed on Cary 5000 UV-Vis-NIR spectrometer. X-ray photoelectron spectroscopy (XPS) measurement is carried out on a Thermo Scientific K-Alpha XPS apparatus equipped with a monochromatic Al K(alpha) source and food gun for charge compensation. To remove the acid residues, the COFs samples are treated with triethylamine methanolic solution, followed by washing with copious amount of methanol and degas at 200° C. under dynamic vacuum for 1 day prior to XPS measurement. Low-dose TEM images of COF-1 are acquired on the TEAM I FEI Titan-class microscope at 300 kV, equipped with both geometric aberrations corrected to third order and chromatic aberrations corrected to the first order. Imaging data are collected in the Gatan K2 direct-detection camera operated in electron-counting mode (camera counting frame rate of 400 fps (frames per second) at 4 k×4 k resolution) with a final image output rate of 40 fps at 4 k×4 k resolution. The HRTEM image of MF-1a is acquired with an FEI TitanX 60 300 microscope at 200 kV. The COF sample is sonicated in toluene with a sonication probe for 15 min and drop-casted onto a copper grid (Lacey C only, 300 mesh Cu). SEM images are obtained with a Zeiss Gemini Ultra-55 Analytical Field Emission Scanning Electron Microscope operated at 15 kV using an in-lens detector. Water contact angle measurements are carried out using a Kruss easy drop optical contact angle meter (Model: FM41) under ambient conditions.

Crystal Structure Modeling

Since the framework structures of MF-1a-e are quite similar, and those of MF-2a-e are close as well, thus only MF-1a and MF-2a are selected as representative examples for structure modeling. The crystal models for MF-1a and MF-2a including the cell parameters and the atomic positions are produced by Materials Studio 5.0 software package1 employing the Crystal Building module. The Pawley PXRD refinement is conducted using the Reflex module in the Materials Studio 5.0, in which a Pseudo-Voigt profile function is employed for whole profile fitting (peak broadening, peak asymmetry, and zero shift error are taken into account). Unit cell and sample parameter are refined simultaneously. The Pawley refinement results including unit cell parameters and final related refinement factors for MF-1a and MF-2a.

Synthesis of COF-1

An o-dichlorobenzene/n-butanol (1 mL/1 mL) mixture of 1,3,5-tri-(4-aminophenyl) benzene (56 mg, 0.16 mmol) and 2,5-dimethoxy terephthalaldehyde (46 mg, 0.24 mmol) in the presence of acetic acid (6 M, 0.2 mL) in a Biotage microwave vial (5 mL) is degassed through 3 freeze-pump-thaw cycles. The vial is sealed and heated at 120° C. for 3 days. The precipitate is collected via centrifugation, washed times with anhydrous THF and subjected to Soxhlet extraction using THF as the solvent for 1 day. The powder collected is dried at 120° C. under vacuum overnight to give yellow colored COF-1 in an isolated yield of ~80%.

Synthesis of COF-2

Benzidine (64 mg, 0.2 mmol) and 1,3,5-triformylbenzene (32 mg, 0.15 mmol) are dissolved via sonication in a mixture of 1,4-dioxane/mesitylene (1 mL/1 mL) in a 5 mL-Biotage microwave vial. Afterwards, aqueous acetic acid (6 M, 0.2 mL) is added to the mixture. The vial is degassed by three freeze-pump-thaw cycles. Finally, the vial is sealed and heated in an oven at 120° C. for 3 days. The precipitates are isolated by centrifugation, washed with anhydrous THF for three times, and dried at 120° C. under vacuum overnight to give a yellow colored powder in ~90% yield.

Synthesis of MFs via Povarov reaction

COFs (4 mg), phenylacetylene (6 µL, 0.05 mmol), $BF_3 \cdot OEt_2$ (4 µL, 0.03 mmol), chloranil (8 mg, 0.03 mmol), and 2 mL of toluene are added to a 5 mL-Biotage microwave vial. The vial is sealed and heated under $N_2$ at 110° C. in an oil bath. After 1-3 days, the mixture is cooled to room temperature and the precipitate is isolated via centrifugation. The reaction mixture is then washed with THF and quenched with saturated aqueous sodium bicarbonate (2 mL×3). Subsequently, the solids are washed with THF using a Soxhlet extractor for 12 h and dried under vacuum.

Chemical stability test of MF-1a

The MF-1a sample (~2 mg) is kept for pre-designed time under static condition in 0.5 mL of 98% triflic acid (2% catalytic $H_2O$) at ambient temperature, 0.5 mL HCl (1 and 12 M) at ambient temperature, 50° C. or 100° C., NaOH (1 and 14 M) in $H_2O$/methanol solution at 60° C. or 100° C., $NaBH_4$ (5 equiv. per imine functionality in MF-1a) in methanol at 60° C. and $KMnO_4$ (5 equiv. per imine functionality in MF-1a) in $H_2O/CH_3CN$ solution. The samples are washed with THF for three times, dried under vacuum at ambient temperature and subjected to PXRD measurements.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A covalent organic framework (COF) comprising a quinoline group having the chemical structure:

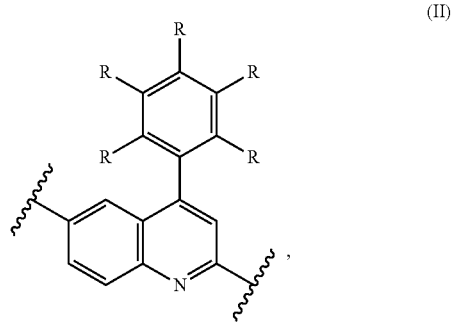

(II)

wherein each R is independently —H, —COOR1, —CHO, —X, —CN, - or R1, wherein each R1 is independently a straight or branched substituted or unsubstituted alkyl chain, and X is a halogen.

2. The COF of claim 1, wherein the COF does not comprise any imine group.

3. The COF of claim 1, wherein the quinolone group has the chemical structure:

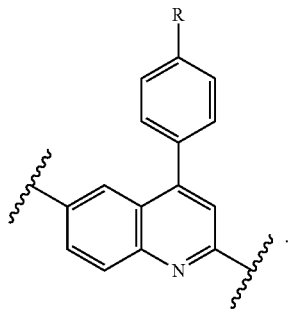

(IIa)

4. A superhydrophobic material comprising: an exposed surface comprising the covalent organic framework (COF) of claim 1; wherein the exposed surface has a water contact angle of equal to or more than about 90°.

5. The superhydrophobic material of claim 4, wherein the superhydrophobic material is freestanding, or the superhydrophobic material is a surface coating on a substrate.

6. The superhydrophobic material of claim 5, wherein the substrate is selected from the group consisting of glass, metal, plastic, paper, wood, concrete and masonry.

7. The superhydrophobic material of claim 5, wherein the substrate is selected from the group consisting of a windshield, a glass plate, a metal plate, a metal object and a glove.

8. The superhydrophobic material of claim 4, wherein the superhydrophobic material has a water contact angle of equal to or more than about 120°.

9. The superhydrophobic material of claim 8, wherein the superhydrophobic material has a water contact angle from about 125° to about 155°.

* * * * *